United States Patent [19]

Walker et al.

[11] 4,154,849

[45] May 15, 1979

[54] N-CYANO-2-(SUBSTITUTED PHENOXY) BUTYRAMIDES AND THEIR USE AS MILDEWICIDES

[75] Inventors: Francis H. Walker, Mill Valley; Don R. Baker, Orinda, both of Calif.

[73] Assignee: Stauffer Chemical Company, Westport, Conn.

[21] Appl. No.: 845,513

[22] Filed: Oct. 26, 1977

[51] Int. Cl.$^2$ .................. A61K 31/26; A61K 31/275; C07C 121/78; C07C 161/02
[52] U.S. Cl. .................................. 424/302; 260/454; 260/465 D; 424/304
[58] Field of Search .......................... 260/465 D, 454; 424/304, 302

[56] References Cited

U.S. PATENT DOCUMENTS

| 2,927,126 | 3/1960 | Pursglove | 260/465 D |
| 3,439,018 | 4/1969 | Brookes et al. | 260/465 D |
| 3,932,168 | 1/1976 | Stein et al. | 260/465 D |
| 4,001,427 | 1/1977 | Baker et al. | 260/465 D |
| 4,052,432 | 10/1977 | Baker et al. | 260/465 D |

*Primary Examiner*—Dolph H. Torrence
*Attorney, Agent, or Firm*—Michael J. Bradley

[57] ABSTRACT

N-cyano-2-(substituted phenoxy) butyramide compounds having the formula

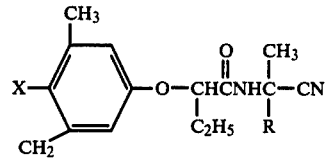

in which X is selected from the group consisting of chlorine, bromine, thiocyano and methyl and R is selected from the group consisting of methyl, ethyl and methoxymethyl and their use as mildewicides for controlling the growth of mildew are disclosed.

27 Claims, No Drawings

N-CYANO-2-(SUBSTITUTED PHENOXY) BUTYRAMIDES AND THEIR USE AS MILDEWICIDES

BACKGROUND OF THE INVENTION

N-dimethylacetonitrilo-α-(substituted phenoxy) alkyl amides and their use as miticides are disclosed in the prior art in U.S. Pat. No. 4,001,427, which was issued to Don R. Baker and Francis H. Walker on Jan. 4, 1977. These compounds differ substantially from the compounds of the present invention in both their utility and substitution of the phenoxy moiety. Such substitution or change in substitutions would not be expected from the disclosure of applicants' prior patent. A further disclosure of compounds similar to applicants' novel compounds is that of U.S. Pat. No. 3,557,209 to Sydney B. Richter et al. That disclosure again fails, as applicants' own prior disclosure fails, to disclose the novel utility of appicants' compounds or applicants' specific substituted phenoxy moiety.

BRIEF DESCRIPTION OF THE INVENTION

This invention relates to N-cyano-2-(substituted phenoxy) butyramides having the formula

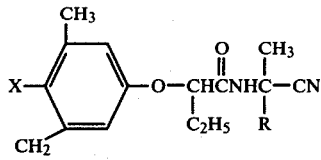

in which X is selected from the group consisting of chlorine, bromine, thiocyano and methyl and R is selected from the group consisting of methyl, ethyl and methoxymethyl and to their utility as mildewicides for controlling the growth of mildew when used in a mildewicidally effective amount. The compounds of this invention are prepared by conventional reactions using the properly selected starting materials and can be applied by conventional techniques.

DETAILED DESCRIPTION OF THE INVENTION

This invention relates to N-cyano-2-(substituted phenoxy) butyramides having the formula

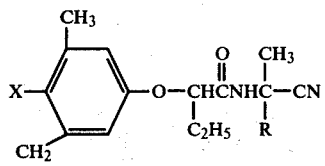

in which X is selected from the group consisting of chlorine, bromine, thiocyano and methyl and R is selected from the group consisting of methyl, ethyl and methoxymethyl, X is preferably selected from the group consisting of chlorine, bromine and methyl and most preferably selected from the group consisting of chlorine and methyl. R is preferably selected from the group consisting of methyl and methoxymethyl and to their utility as mildewicides for controlling the growth of mildew when used in a mildewicidally effective amount.

The term "mildewicide" as used herein refers to a compound which is useful for controlling the growth of fungi, referred to as mildew. Controlling the growth of mildew by applying the compounds described herein can be accomplished by applying a mildewicidally effective amount to the environment in which the growth of mildew fungi is encouraged. The compounds may be applied to any environmental area which supports the growth and development of mildew fungi. By "controlling" is meant the prevention of the growth of the mildew fungi to be controlled.

The novel compounds of this invention may generally be prepared as follows:

1. Preparation of a 3,4,5-trisubstituted phenoxy alkanoic acid

A 3,4,5-trisubstituted phenol is reacted with a halo-substituted aliphatic acid of the formula

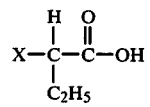

in which X is Cl or Br in the presence of sodium hydroxide at a temperature of from about 40° to about 110° C. to produce the corresponding 2-(3,4,5-trisubstituted) phenoxy alkanoic acid.

2. Preparation of a 3,4,5-trisubstituted phenoxy alkanoic acid chloride

The acid prepared in step 1 above is reacted with phosgene at a temperature of from about 40° C. to about 70° C. in the presence of dimethyl formamide as a catalyst to produce the corresponding 3,4,5-trisubstituted phenoxy alkanoic acid chloride.

3. Preparation of the 3,4,5-trisubstituted phenoxy alkanoic amides of this invention The acid chloride prepared in step 2 above is reacted with an amine of the formula

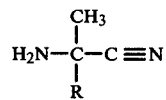

wherein R is methyl, ethyl or methoxymethyl in the presence of sodium hydroxide or an organic base such as triethyl amine in a solvent such as methylene chloride at a temperature of from about −15° C. to about 35° C. to produce the desired amide.

An alternative method of preparation is to react an α-halosubstituted aliphatic acid of the formula

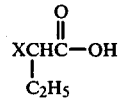

in which X is Cl or Br with phosgene and dimethyl formamide catalyst to produce the corresponding acyl chloride of the formula

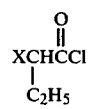

in which X is Cl or Br which in turn is reacted with an amine of the formula

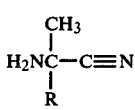

wherein R is methyl, ethyl or methoxymethyl in the presence of an organic base such as triethylamine to produce the corresponding α-haloalkylamide.

This amide is reacted with the sodium salt of a phenol of the formula

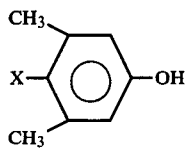

wherein X is chlorine, bromine, thiocyano or methyl prepared by the reaction of this phenol and sodium hydride in tetrahydrofuran as solvent to give the subject amides.

The following examples demonstrate preparation of the novel compounds and utility in controlling mildew fungi.

EXAMPLE I

N-Dimethylacetonitrilo-2-(4-Chloro-3,5-Dimethylphenoxy) Butyramide a. 50 grams (0.32 mole) of 4-chloro-3,5-dimethylphenol were mixed with 58.5 grams (0.35 mole) of 2-bromobutyric acid in a 500 milliliter flask equipped with stirring equipment maintained at a temperature of 15° C. 60.8 grams (0.76 mole) of 50% aqueous sodium hydroxide were added to the mixture with rapid stirring. The temperature rose to 45° C. over the course of the addition and was held below 45° C. with a cold bath. After all the sodium hydroxide had been added, cooling was terminated and the mixture was heated at 110° C. for 15 minutes. Then some water, 80 milliliters of perchloroethylene and 65 milliliters of concentrated HCl were added with stirring, the mixture was heated to 85° C., phase-separated and the organic layer was cooled. The product, which was identified by analysis of nuclear magnetic resonance spectra as 2-(4-chloro-3,5-dimethyl phenoxy) butyric acid, separated as a solid which was removed by filtration and air dried to give 60.7 grams (78% yield) of product having a melting point of 99°-102° C.

b. 57.4 grams (0.24 mole) of the acid produced in step a. above were slurried in 150 milliliters of toluene in a 500 milliliter flask fitted with a gas-inlet tube, stirrer, thermometer, and dry ice/isopropyl alcohol condenser. 0.2 milliliter of dimethyl formamide was added and the mixture was heated to 60° C. Phosgene was passed into the mixture at a moderate rate until 30 grams (0.31 mole) had been added. At the conclusion of the phosgene addition, the dry ice condenser was removed and replaced with a water-cooled condenser. Excess phosgene and hydrogen chloride were removed by purging with argon at 60° C. 60.7 grams (96% yield) of a product, which was identified by analysis of nuclear magnetic resonance spectra as 2-(4-chloro-3,5-dimethylphenoxy) butyryl chloride, was recovered as an oil from the solution by cooling the solution and removing the solvent under vacuum.

c. 8 Grams (0.03 mole) of the acyl chloride prepared in step b. above were added dropwise to a 300 milliliter flask containing a stirred solution of 2.9 grams (0.04 mole) α-aminoisobutyronitrile and 3.5 grams (0.04 mole) triethyl amine in 100 milliliter of methylene chloride at 10°-15° C. Some cooling was necessary to maintain the temperature. After all the acyl chloride was added, the mixture was allowed to come to room temperature and the product was isolated by sequentially washing with 100 milliliters each of water, dilute HCl, 5% $Na_2CO_3$ solution and water. The organic phase was dried over magnesium sulfate and the solvent was removed in vacuum to leave 9.0 grams (97% yield) of a solid having a melting point of 108°-110° C. The product was identified as the title compound by analysis of nuclear magnetic resonance spectra.

EXAMPLE II

N-(1-Cyano-1-Methyl-2-Methoxymethyl)-2-(4-Chloro-3,5-Dimethylphenoxy) Butyramide 8.0 grams (0.03 mole) of the acyl chloride prepared as in Example Ib was added dropwise, as in Example Ic, to a stirred mixture of 4.5 grams (0.03 mole) of 1-cyano-1-methyl-2-methoxy ethyl amine hydrochloride, 4.8 grams (0.06 mole) 50% aqueous sodium hydroxide, 15 milliliters water and 90 milliliters methylene chloride at 10°-15° C. The mixture was allowed to come to room temperature after addition was complete. The material was isolated as in Example Ic to give 2.0 grams of a solid, which when recrystallized from ethanol, had a melting point of 120°-127° C. The product was identified as the title compound by analysis of nuclear magnetic resonance spectra. The yield was 20%.

EXAMPLE III

N-Dimethylacetonitrilo-2-(4-Bromo-3,5-Dimethyl Phenoxy) Butyramide a. 4-bromo-3,5-dimethylphenoxy butyric acid, which was identified by analysis of nuclear magnetic resonance spectra, was prepared as in Example I but using:
  18 grams (0.09 mole) 4-bromo-3,5-dimethylphenol,
  18 grams (0.11 mole) 2-bromobutyric acid and
  18.4 grams (0.23 mole) 50% NaOH
The only difference in the work-up was that 20 milliliters of water, 50 milliliters of perchloroethylene and 20 milliliters of concentrated HCl were used. 21.3 grams of the acid having a melting point of 78°-85° C. was produced. Yield was 82% of theory.

b. 4-bromo-3,5-dimethylphenoxy butyryl chloride was prepared as in Example Ib but using:
  21.3 grams acid (0.07 mole),
  10.0 grams phosgene (0.10 mole),
  50 milliliters of toluene and
  0.2 milliliters of dimethyl formamide
to yield 21.3 grams of the butyryl chloride as an oil.

c. N-dimethylacetonitrilo-2-(4-bromo-3,5-dimethylphenoxy) butyramide, which was identified by analysis of nuclear magnectic resonance spectra, was then prepared as in Example Ic, but using
  80 grams acyl chloride (0.03 mole),
  4.0 grams α-aminoisobutyronitrile, 85% pure (0.04 mole) and
  4.0 grams triethylamine (0.04 mole)
in 100 milliliters of benzene as the reaction solvent to yield 6.5 grams of a solid having a melting point of 83°-87° C. The yield was 61% of theory.

EXAMPLE IV

N-Dimethylacetonitrilo-2-(3,4,5-Trimethylphenoxy) Butyramide a. 2-(3,4,5-trimethylphenoxy) butyric acid, which was identified by analysis of nuclear magnetic resonance spectra, was prepared as in Example Ia only using:
 50 grams (0.37 mole) 3,4,5-trimethylphenol,
 74 grams (0.44 mole) 2-bromobutyric acid and
 76.1 grams (0.95 mole) 50% aqueous sodium hydroxide
The product was worked up in the same manner with:
 90 milliliters $H_2O$,
 90 milliliters perchloroethylene and
 90 milliliters concentrated HCl
51.0 grams of the acid having a melting point of 55°–64° C. was produced. The yield was 62% of theory.

b. 2-(3,4,5-trimethylphenoxy) butyryl chloride, which was identified by analysis of nuclear magnetic resonance spectra, was prepared as in Example Ib only using:
 51 grams acid (0.23 mole),
 27 grams phosgene (0.28 mole),
 150 milliliters toluene and
 2 milliliters dry dimethylformamide
to give acyl chloride, 52.0 grams (94% yield) to yield 52.0 grams of the butyryl chloride.

c. N-dimethylacetonitrilo-2-(3,4,5-trimethylphenoxy) butyramide, which was identified by analysis of nuclear magnetic resonance spectra, was prepared as in Example Ic but using:
 7.2 grams (0.03 mole) acid chloride,
 2.5 grams (0.03 mole) α-aminoisobutyronitrile,
 3.0 grams (0.03 mole) triethylamine and
 100 milliliters toluene
as a reaction solvent to yield 5.1 grams of a solid having a melting point of 94°–98° C. The yield was 58% of theory.

In the following table, the above four examples are listed together with three additional examples which were prepared in a manner analogous to that described above, starting with the appropriate materials. The compounds in the table are representative of those embodied in the present invention. Compound numbers are assigned to each compound and are used through the remainder of the application.

TABLE 1

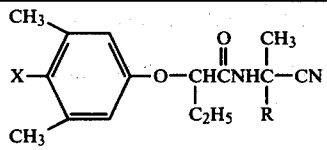

| Compound Number | X | R | Physical Properties |
|---|---|---|---|
| 1 | —Cl | —CH₃ | m.p. 108–110° C. |
| 2 | —Cl | —CH₂OCH₃ | m.p. 120–127° C. |
| 3 | —Br | —CH₃ | m.p. 83–87° C. |
| 4 | —CH₃ | —CH₃ | m.p. 94–98° C. |
| 5 | —Cl | —CH₂CH₃ | m.p. 89–93° C. |
| 6 | —SCN | —CH₃ | m.p. 127–132° C. |

FOLIAR FUNGICIDE EVALUATION TESTS

Evaluation for Preventive Action on Bean Powdery Mildew

A candidate chemical is dissolved in an appropriate solvent and diluted with water containing several drops of Tween 20 ®, a polyoxyethylene sorbitan monolaurate wetting agent. Test concentrations, ranging from 1000 parts per million downward, are sprayed to runoff on the primary leaves of pinto beans (*Phaseolus vulgaris L.*). After the plants are dry, the leaves are dusted with spores of the powdery mildew fungus (*Erysiphe polygoni* De Candolle) and the plants are retained in the greenhouse until the fungal growth appears on the leaf surface. Effectiveness is recorded as the lowest concentration, in parts per million, which will provide 50% reduction in mycelial formation as compared to untreated, inoculated plants. These values are recorded in Table II.

Table II

| | Preventive Action |
|---|---|
| Compound Number | Bean Powdery Mildew |
| 1 | 25 |
| 2 | 5 |
| 3 | 50 |
| 4 | 5 |
| 5 | 500 |
| 6 | 1000 |

The compounds of this invention are generally embodied into a form suitable for convenient application. For example, the compounds can be embodied into pesticidal compositions which are provided in the form of emulsions, suspensions, solutions, dusts and aerosol sprays. In general, such compositions will contain, in addition to the active compound, the adjuvants which are found normally in pesticide preparations. In these compositions, the active compounds of this invention can be employed as the sole pesticide component or they can be used in admixture with other compounds having similar utility. The pesticide compositions of this invention can contain, as adjuvants, organic solvents, such as sesame oil, xylene range solvents, heavy petroleum, etc.; water; emulsifying agents; surface active agents; talc; pryophyllite; diatomite; gypsum; clays, propellants, such as dichlorodifluoromethane, etc. If desired, however, the active compounds can be applied directly to feedstuffs, seeds, etc., upon which the pests feed. When applied in such a manner, it will be advantageous to use a compound which is not volatile. In connection with the activity of the presently disclosed pesticidal compounds, it should be fully understood that it is not necessary that they be active as such. The purposes of this invention will be fully served if the compound is rendered active by external influences, such as light or by some physiological action which occurs when the compound is ingested into the body of the pest.

The precise manner in which the pesticidal compositions of this invention are used in any particular instance will be readily apparent to a person skilled in the art. Generally, the active pesticide compound will be embodied in the form of a liquid composition; for example, an emulsion, suspension, or aerosol spray. While the concentration of the active pesticide in the present compositions can vary within rather wide limits, ordinarily the pesticide compound will comprise not more than about 15.0% by weight of the composition. Preferably, however, the pesticide compositions of this invention will be in the form of solutions or suspensions containing about 0.1 to 1.0% by weight of the active pesticide compound.

What is claimed:
1. A compound having the formula

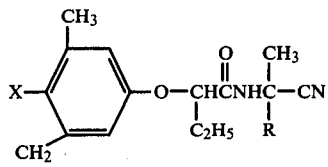

in which X is selected from the group consisting of chlorine, bromine, thiocyano and methyl and R is selected from the group consisting of methyl, ethyl and methoxymethyl.

2. The compound of claim 1 in which X is selected from the group consisting of chlorine, bromine and methyl and R is selected from the group consisting of methyl and methoxymethyl.

3. The compound of claim 1 in which X is selected from the group consisting of chlorine and methyl and R is selected from the group consisting of methyl and methoxymethyl.

4. The compound of claim 1 in which X is chlorine and R is methyl.

5. The compound of claim 1 in which R is methoxymethyl.

6. The compound of claim 1 in which X is bromine and R is methyl.

7. The compound of claim 1 in which X is methyl and R is methyl.

8. The compound of claim 1 in which X is chlorine and R is ethyl.

9. The compound of claim 1 in which X is thiocyano and R is methyl.

10. A composition of matter comprising a mildewicidally effective amount of the compound having the formula

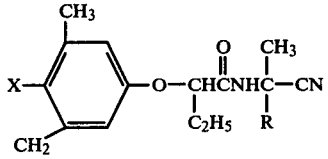

in which X is selected from the group consisting of chlorine, bromine, thiocyano and methyl and R is selected from the group consisting of methyl, ethyl and methoxymethyl and an inert carrier.

11. The composition of claim 10 wherein X is selected from the group consisting of chlorine, bromine and methyl and R is selected from the group consisting of methyl and methoxymethyl.

12. The composition of claim 10 wherein X is selected from the group consisting of chlorine and methyl and R is selected from the group consisting of methyl and methoxymethyl.

13. The composition of claim 10 wherein X is chlorine and R is methyl.

14. The composition of claim 10 wherein R is methoxymethyl.

15. The composition of claim 10 wherein X is bromine and R is methyl.

16. The composition of claim 10 wherein X is methyl and R is methyl.

17. The composition of claim 10 wherein X is chlorine and R is ethyl.

18. The composition of claim 10 wherein X is thiocyano and R is methyl.

19. A method of controlling the growth of mildew comprising applying to the locus thereof a mildewicidally effective amount of a compound having the formula

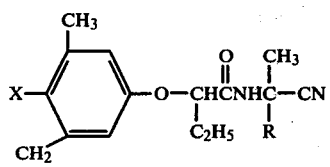

in which X is selected from the group consisting of chlorine, bromine, thiocyano and methyl and R is selected from the group consisting of methyl, ethyl and methoxymethyl.

20. The method of claim 19 wherein X is selected from the group consisting of chlorine, bromine and methyl and R is selected from the group consisting of methyl and methoxymethyl.

21. The method of claim 19 wherein X is selected from the group consisting of chlorine and methyl and R is selected from the group consisting of methyl and methoxymethyl.

22. The method of claim 19 wherein X is chlorine and R is methyl.

23. The method of claim 19 wherein X is methoxymethyl.

24. The method of claim 19 wherein X is bromine and R is methyl.

25. The method of claim 19 wherein X is methyl and R is methyl.

26. The method of claim 19 wherein X is chlorine and R is ethyl.

27. The method of claim 19 wherein X is thiocyano and R is methyl.

* * * * *

UNITED STATES PATENT AND TRADEMARK OFFICE
CERTIFICATE OF CORRECTION

PATENT NO. : 4,154,849
DATED : May 15, 1979
INVENTOR(S) : Francis H. Walker and Don R. Baker It is certified that error appears in the above-identified patent and that said Letters Patent are hereby corrected as shown below:

Please correct the formulas in the ABSTRACT; under BRIEF DESCRIPTION OF THE INVENTION, Column 1; under DETAILED DESCRIPTION OF THE INVENTION, Column 1; under Claim 1, Column 7; under Claim 10, Column 7 and under Claim 19, Column 8 as follows:

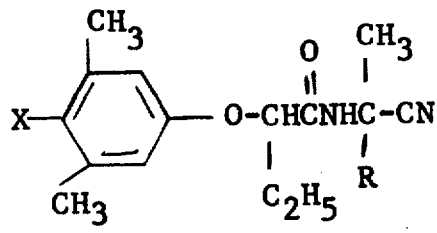

Signed and Sealed this

Third Day of June 1980

[SEAL]

Attest:

SIDNEY A. DIAMOND

Attesting Officer      Commissioner of Patents and Trademarks